US 6,719,907 B2
Apr. 13, 2004

(54) DUAL-STAGE FILTRATION CARTRIDGE

(75) Inventors: Gregory R Collins, Monroe, NY (US); James Summerton, Hillsdale, NJ (US); Edward Spence, Bronx, NY (US)

(73) Assignee: Nephros, Inc., New York, NY (US)

( * ) Notice: Subject to any disclaimer, the term of this patent is extended or adjusted under 35 U.S.C. 154(b) by 88 days.

(21) Appl. No.: 10/021,478

(22) Filed: Oct. 30, 2001

(65) Prior Publication Data

US 2002/0053540 A1 May 9, 2002

Related U.S. Application Data

(60) Provisional application No. 60/244,317, filed on Oct. 30, 2000, and provisional application No. 60/259,889, filed on Jan. 2, 2001.

(51) Int. Cl.[7] .................. B01D 61/00; B01D 61/24; B01D 61/28; B01D 63/00; B01D 63/04

(52) U.S. Cl. ............ 210/646; 210/321.6; 210/321.64; 210/321.72; 210/321.8; 210/321.81; 210/321.88; 210/321.89; 210/321.9

(58) Field of Search ................ 210/645, 646, 210/321.6, 321.64, 321.72, 321.79, 321.8, 321.81, 321.88, 321.89, 321.9

(56) References Cited

U.S. PATENT DOCUMENTS

| | | | |
|---|---|---|---|
| 3,579,441 A | 5/1971 | Brown | |
| 3,878,095 A | 4/1975 | Fraier et al. | 210/87 |
| 3,946,731 A | 3/1976 | Lichtenstein | 128/214 |
| 3,976,576 A | 8/1976 | Jacobsen et al. | 210/321 |
| 4,038,190 A | 7/1977 | Baudet et al. | 210/321 |
| 4,056,467 A | 11/1977 | Christen | 210/23 |
| 4,118,314 A | 10/1978 | Yoshida | 210/22 |
| 4,134,834 A | 1/1979 | Brous | 210/127 |

(List continued on next page.)

FOREIGN PATENT DOCUMENTS

| | | |
|---|---|---|
| EP | 0 018 734 | 11/1980 |
| EP | 0 076 422 | 4/1983 |
| EP | 0 516 152 | 12/1992 |
| EP | 0 890 368 | 1/1999 |
| EP | 0 960 624 | 12/1999 |
| WO | WO 92/11878 | 7/1992 |
| WO | WO 98/16171 | 4/1998 |
| WO | WO 98/16269 | 4/1998 |
| WO | WO 98/30258 | 7/1998 |
| WO | WO 98/50090 | 11/1998 |
| WO | WO 00/06292 | 2/2000 |
| WO | WO 00/25902 | 5/2000 |
| WO | WO 00/44478 | 8/2000 |

OTHER PUBLICATIONS

Albertini, B. von, et al., 2nd Annual Workshop of the International Soeicty of Hemofiltration, Blood Purification 2: 44–64 (1984).

Basile, Carlo et al., Plasma Volume Changes induced by Hypertonic Hemodiafiltration and Standard Hemodialysis, Am. J. Nephrol. 7: 264–269 (1987).

(List continued on next page.)

*Primary Examiner*—John Kim
(74) *Attorney, Agent, or Firm*—Darby & Darby (57) ABSTRACT

A dual-stage filtration cartridge is provided. The cartridge can be embodied as a mid-dilution hemodiafiltration cartridge or a redundant sterilization filtration cartridge. The cartridge includes a housing having a first end and an opposing second end. The housing has a primary fluid inlet and outlet at the first end of the cartridge. The housing also defines first and second filtration stages with the first filtration stage including first filtering elements disposed between the first and second ends of the housing. Each stage has a separate inter-lumen fiber space, but shares a common extra-lumen space. The primary fluid inlet communicates with the first filtering elements at the first end so that fluid flows through the first filtering elements toward the second end. The second filtration stage includes second filtering elements disposed between the first and second ends of the housing with the fluid outlet communicating with the second filtering elements at the first end.

36 Claims, 4 Drawing Sheets

U.S. PATENT DOCUMENTS

| | | | |
|---|---|---|---|
| 4,219,422 A | 8/1980 | Knothe et al. | 210/137 |
| 4,326,955 A | 4/1982 | Babb et al. | 210/638 |
| 4,381,999 A | 5/1983 | Boucher et al. | 210/637 |
| 4,468,329 A | 8/1984 | Shaldon et al. | 210/651 |
| 4,498,990 A | 2/1985 | Shaldon et al. | 210/637 |
| 4,647,378 A | 3/1987 | Minami | 210/646 |
| 4,702,829 A | 10/1987 | Polaschegg et al. | 210/195.2 |
| 4,708,802 A | 11/1987 | Rath et al. | 210/641 |
| 4,770,769 A | 9/1988 | Schael | 210/96.2 |
| 4,784,495 A | 11/1988 | Jonsson et al. | 366/151 |
| 4,834,888 A | 5/1989 | Polaschegg | 210/646 |
| 4,861,485 A | 8/1989 | Fecondini | 210/641 |
| 5,011,607 A | 4/1991 | Shinzato | 210/637 |
| 5,069,788 A | 12/1991 | Radovich et al. | 210/321.8 |
| 5,075,003 A | 12/1991 | Aoyagi | 210/321.8 |
| 5,178,763 A | 1/1993 | Delaunay | 210/644 |
| 5,194,157 A | 3/1993 | Ghezzi et al. | 210/646 |
| 5,244,568 A | 9/1993 | Lindsay et al. | 210/87 |
| 5,431,811 A | 7/1995 | Tusini et al. | 210/90 |
| 5,476,592 A | 12/1995 | Simard | 210/651 |
| 5,487,827 A | 1/1996 | Peterson et al. | 210/87 |
| 5,660,722 A | 8/1997 | Nederlof | 210/90 |
| 5,690,831 A | 11/1997 | Kenley et al. | 210/646 |
| 5,700,372 A | 12/1997 | Takesawa et al. | 210/321.81 |
| 5,702,597 A | 12/1997 | Chevallet et al. | 210/195.2 |
| 5,725,775 A | 3/1998 | Bene et al. | 210/646 |
| 5,744,042 A | 4/1998 | Stange et al. | 210/645 |
| 5,808,181 A | 9/1998 | Wamsiedler et al. | 73/38 |
| 5,846,419 A | 12/1998 | Nederlof | 210/323.1 |
| 5,882,516 A | 3/1999 | Gross et al. | 210/321.6 |
| 5,942,112 A | 8/1999 | Ishak | 210/321.6 |
| 6,315,895 B1 * | 11/2001 | Summerton et al. | 210/96.2 |

OTHER PUBLICATIONS

Basile, Carlo et al., Hypertonic hemodiafiltration: A preliminary report on a cross–over study, Kidney International, vol. 33, Suppl. 24, pp. S–132–S–134 (1988).

Canaud, B,. et al., Hemodiafiltratyion with On–Line Production of substitution Fluid: Long–Term Safety and Quantitative Assessment of Efficacy, Maeda K. Shinzato T (eds): Effective Hemodiafiltration: New Methods. Contrib Nephrol. Basel, Karger, vol. 108. pp 12–22 (1994).

Ghezzi, P.M. et al., Hemodiafiltration Without Replacement Fluid, ASAIO Journal, 61–65 (1992).

Ghezzi, P.M. et al., Use of the ultrafiltrate obtained in two–chamber (PFD) hemodiafiltration as replacement fluid. Experimental ex vivo and in vitro study. The International Journal of Artificial Organs/ vol. 14/no. 6, 1991/pp. 327–334.

Kim, Sung–Teh, Characteristics of Protein Removal in Hemodiafiltration, Maeda K. Shinzato T (eds): Effective Hemodiafiltration: New Methods. Contrib Bephrol. Basel, Karger, vol. 108, pp. 23–37, (1994).

Limido, D. et al., Clinical evaluation of AK 100 ULTRA for predilution HF with on–line prepared bicarbonate substitution fluid. Comparison with HD and acetate postdilution HF. The International Journal of Artificial Organs/vol. 20/no. 3, 1997/pp. 153–157.

Maeda, Kenji, et al., Push/Pull Hemodiafiltration: Technical Aspects and Clinical Effectiveness, Nephron 71: 1–9 (1995).

Man, N. K., et al., Acetate–Free Biofiltration: State of the Art, Hemodiafiltration: New Methods. Contib Nephrol. Basel, Karger, vol. 108, pp. 87–93 (1994).

Maragoni Roberto, et al., Short Time Treatment with high–efficiency Paired Filtration Dialysis for Chronic Renal Failure, Artificial Organs, 547–552, Blackwell Scientific Publications, Inc., Boston International Society for Artificial Organs (1992).

Miller, J. H., et al., Technical Aspects of High–Flux Hemodiafiltration for Adequate short (Under 2 Hours) Treatment, Department of Medicine, Wadsworth V.A. medical Center, and UCLA school of; medicine, Los Angeles, California, pp. 377–380 (1984).

Ono Masataka, et al. Comparison of Types of On–Line Hemodiafiltration from the Standpoint of Low–Molecular–Weight Protein Removal, Contrib Nephrol. Basel, Karger, vol. 108. pp. 38–35 (1994).

Polaschegg Hans–Dietrich, et al., Hemodialysis Machines and Monitors, pp 333–379, (undated).

Ronco, C. et al., Comparison of four different short dialysis techniques. The International Journal of Artificial Organs/ vol. 11/no. 3, pp 169–174, (1998).

Ronco, C. et al., Paired Filtration dialysis: Studies on Efficiency, Flow Dynamics and Hydraulic Properties of the System, Blood Purif 8: 126–140, (1990).

Ronco, C. et al., Technical and Clinical Evaluation of Different short, Highly Efficient Dialysis Techniques, Contr. Nephrol., vol. 61, pp. 46–68 (Karger, Basel 1998).

Rotellar Emilio, Large–Surface Hemodialysis, Artificial Organs, 387–396, Raven Press, New York, International society for Artificial Organs, (1986).

Sanz–Moreno C. et al., Hemodiafiltration in Two Chambers Without Replacement Fluid: A Clinical Study. Artificial Organs, 19(5): 407–410, Blackwell Science, Inc., Boston International Society for Artificial Organs (1995).

Shaldon S., Mixed Hemofitration (HMF): 18 Months Experience With Ultrashort Treatment Time, vol. XXV11 Trans Am Soc Artif Intern Organs, pp. 610–612, (1981).

Shinaberger James H. et al., Short Treatment 16: pp. 360–381, (undated).

Shinzato, et al., Newly Developed Economical and Efficient Push/Pull Hemodiafiltration, Maeda K. Shinzato T (eds): Effective Hemodiafiltration: New Methods. Contrib Nephrol Basel, Karger, vol. 108, pp. 79–86 (1994).

Sternby Jan, A Decade of Experience with On–Line Hemofiltration/Hemodiafiltration, Maeda K. Shinzato T (eds): Effective Hemodiafiltration: New Methods. Contrib Nephrol Basel, Karger, vol. 108, pp. 1–11 (1994).

Tsuruta Kazuma, A Simple Method for Clinical Application of Push/Pull Hemodiafiltration, Maeda K. Shinzato T (eds): Effective Hemodiafiltration: New Methods. Contrib Nephrol Basel, Karger, vol. 108, pp. 71–78 (1994).

Usuda M., et al., New Simultaneous HF and HD With No Infusion Fluid, vol. XXV111 Trans Am Soc Artif Intern Organs, pp. 24–25, (1982).

Vanholder, et al., In vivo solute elimination of paired filtration dialysis. The International Journal of Artificial Organs/ vol. 14/ no. 1, pp. 23–27 (1991).

Zucchelli P., Paired Filtration Dialysis: Optimizing Depurative Efficiency with Separate Convection and Diffusion Processes, Nephron 56: 166–173 (1990).

* cited by examiner

DUAL-STAGE FILTRATION CARTRIDGE

CROSS-REFERENCE TO RELATED APPLICATIONS

The present application claims the benefit of U.S. patent application Ser. No. 60/244,317, filed Oct. 30, 2000 and U.S. patent application Ser. No. 60/259,889, filed Jan. 2, 2001, both of which are hereby incorporated by reference in their entirety.

FIELD OF THE INVENTION

The present invention relates to filtration devices and methods and, more particularly, to a filtration cartridge and its uses as a hemodiafilter in one application and a fluid filter that produces sterile fluid in another application.

BACKGROUND OF INVENTION

The most common treatment for End Stage Renal Disease (ESRD) essentially consists of a hemodialysis process, wherein blood to be cleaned flows on one side of a semi-permeable membrane and a physiologic solution, a dialysate, flows on the other side of the membrane, whereby toxins in the blood are transferred from one side to the other. The primary driving force in this treatment is diffusion. This process is generally effective in removing small Molecular Weight (MW) toxins such as urea and creatinine. However, this process is much less effective in removing middle range MW substances, e.g., substances having a molecular weight higher than about 1 kDa, because of a low diffusion coefficient of such substances.

To a much lesser extent hemodiafiltration is used as a treatment modality. In hemodiafiltration, diffusion is combined with filtration to remove toxins from the blood. Sterile non-pyrogenic replacement fluid is added to the blood either prior to or after it enters a hemodiafiltration cartridge. The replacement fluid replaces plasma water, which is filtered across the semi-permeable membrane during the hemodiafiltration process. The advantage of hemodiafiltration over hemodialysis is the use of filtration in conjunction with diffusion to remove toxins. As a result of this combination, hemodiafiltration is more efficient at removing small molecules, e.g., creatinine and urea, as well as removing much greater quantities of middle range MW substances, by filtration.

Two primary needs must be met for hemodiafiltration to be effective. The first is for a patient treatment diafilter that allows for high filtration rates and as a result increased clearances of toxins. The second is for a sterilizing filter or series of filters that can provide large volumes of sterile infusion fluid in a continuous manner.

Regarding the first need, state of the art designs for hemodiafilters are substantially equivalent to those of high flux dialyzers. Such filters consist of a bundle of hollow fibers in a cylindrical housing. During operation of the hemodiafiltration system, replacement fluid is injected into the blood either upstream (pre-dilution) or downstream (post-dilution) of the filter cartridge.

Diafiltration devices using pre-dilution or post-dilution schemes have inherent efficiency limitations. Pre-dilution schemes allow for relatively unlimited filtration, however, because the blood is diluted prior to reaching the filter, the overall mass transfer of solutes by diffusion is decreased. In other words, the efficiency of the removal of the toxins is less than desired. Post-dilution schemes have the advantage of keeping blood concentrations high, resulting in more efficient diffusion and convection of solutes, however, the increased concentration of blood cells and the resultant higher blood viscosity during filtration, poses a limit on the amount of water that can be filtered. This is typically limited to approximately 25% of the blood flow.

With respect to the second need, hemodiafiltration requires large volumes of sterile infusion fluid be available, therefore the standard methodology of IV infusion (hanging one liter saline bags) is not appropriate. Instead a method in which sterile fluid is produced in a continuous manner is generally required to satisfy this need.

There are methods where non-sterile infusion fluid for hemodiafiltration is filtered through one or a series of filters to render it sterile before infusion into the patient's bloodstream. The filtration arrangement in these processes must remove endotoxins, bacteria, and other pyrogen-inducing compounds. If a filter should fail during the process, a patient may suffer a septic or pyrogenic reaction due to inadequately filtered fluid.

Several filtration techniques and devices do currently exist. For example on-line production of substitution fluid is described in D. Limido, et al., "*Clinical Evaluation of AK-100 ULTRA for Predilution HF with On-Line Prepared Bicarbonate Substitution Fluid. Comparison with HD and Acetate Postdilution HF*", International Journal of Artificial Organs, Vol. 20, No. 3 (1997), pp. 153–157. Another sterility filter is described in U.S. Pat. No. 4,784,768 to Mathieu. Most prior art schemes have key drawbacks, they either rely on a single filter to sterilize the fluid or they use two separate filters in series increasing the cost and complexity.

The need exists for a filter that provides redundant sterile filtration and produces physiologic fluid suitable for patient infusion.

SUMMARY OF INVENTION

In attempting to meet the first need of providing a diafilter that accommodates high filtration rates, one embodiment of the diafilter reduces and/or eliminates the drawbacks of prior art hemodiafiltration devices by providing a scheme in which blood is diluted after it is partially, but not fully, diafiltered. The diafiltration scheme of the present invention combines the benefits of pre-dilution schemes, e.g., high filtration rates, with the benefits of post-dilution schemes, e.g., high diffusive and convective efficiencies. The present diafilter can be adapted to operate in conjunction with conventional diafiltration machines, including but not limited to Fresenius 4008 On-Line Plus, Gambro AK 200 Ultra. Alternatively, the diafilter may be used with conventional hemodialysis machines, including but not limited to, Fresenius 2008H, Baxter SPS 1550, Cobe Centry System 3, etc, that have been modified to provide a source of replacement fluid. For example, a pump or valve meters dialysate from a tee in the main dialysate stream and passes it through sterilizing filters.

When serving as a diafiltration cartridge, the present invention has blood and dialysate inlet and outlet ports. The cartridge includes a single housing, for example, a cylindrical housing, which houses two hemodiafiltration stages, wherein the first stage has a blood inlet and the second stage has a blood outlet. Accordingly, the present invention accomplishes dual-stage diafiltration within a single cylindrical housing having a cylindrical hollow fiber bundle disposed therein. The diafilter thus has the appearance of a traditional dialyzer with the exception that the construction of its two ends or header caps differs from that of a traditional dialyzer design. The first end cap includes both the blood inlet and blood outlet ports separated by an internal wall and seal, which is designed to segregate the filter into first and second diafiltration stages. The second end cap serves as blood/replacement fluid mixing chamber and has an inlet port for receiving substitution fluid.

In the diafilter embodiment of the present invention, the blood inlet and outlet ports are located at a first end of the cartridge. The dialysate outlet is preferably also located at or near the first end of the cartridge. For example, in one exemplary embodiment, the blood inlet and outlet ports and dialysate outlet are located at the top (first end) of the cartridge. The main cylindrical housing contains a longitudinal bundle of high flux semi-permeable hollow fibers sealed off from the dialysate compartments at each end by a potting compound, such as polyurethane. The substitution fluid inlet and the dialysate inlet are located at or near an opposite second end, e.g., the bottom of the cartridge. At the substitution fluid inlet port a sterile replacement fluid is mixed with the partially diafiltered blood. This occurs in a common header region where the blood exits the hollow fibers of the first stage and enters the hollow fibers of the second stage. The dialysate flow is common to the two filter stages and runs counter-current to blood flow in the first stage and co-current to blood flow in the second stage.

The counter-current flow in the first stage keeps a maximum concentration gradient of uremic toxins allowing for high diffusive clearance of small molecular weight (MW) solutes. The co-current dialysate flow in the second stage necessitated by the design of the present cartridge, is acceptable because convective clearances dominate diffusive clearances in this stage. The relative filtration rates of the first and second stages are passively controlled by the effect that hemodilution and hemoconcentration have on the resistance to flow across the membrane in these stages.

After the blood flows through the hollow fibers of the second stage, the blood exits the diafilter through the blood outlet port located at the same end as the blood inlet port.

Another embodiment of the present invention seeks to meet the second need of providing large volumes of sterile infusion fluid. It addresses the shortcomings of prior art by providing serial (redundant) filtration within a single cartridge and single fiber bundle. As a result of the redundancy there is added assurance of sterility and the removal of endotoxin. Due to the single bundle design there is greater simplicity and convenience compared to current state of the art.

The sterility filter embodiment of the cartridge is similar in appearance and function to the diafiltration embodiment with a few exceptions. The sterility filter has a single cylindrical housing with a cylindrical hollow fiber bundle disposed therein. However, only one end cap is necessary for the sterility filter. The cap is a two-port cap with a non-sterile fluid inlet port and sterile fluid outlet port separated by an internal wall and seal that also segregates the filter into primary and redundant filtration stages. At the other end of the device the fiber remains encased with the ends sealed in the potting compound. As a result of this dead-end filtration configuration there is no need for a second end cap.

In the sterility filter embodiment of the cartridge the fluid inlet and outlet ports are located at one end of the device, for example the top. The fluid may be dialysate, which is drawn off as a portion of the machine dialysate flow with the intent to be used as replacement fluid in diafiltration therapy. The ports that serve as dialysate ports in the diafilter embodiment of the cartridge are normally closed off in the sterility filter embodiment. In this embodiment they may be used for priming, testing, or disinfection of the filter.

During operation non-sterile fluid enters the inlet port and the fibers of the first (primary filtration) stage. Because the fiber lumens are closed at the other end, all the fluid is forcibly filtered across the membrane and into the casing (filtration) space. The membrane in this embodiment is such that during filtration it removes endotoxin and all bacteria from the fluid rendering it as sterile infusion quality fluid. The common casing space between the two filtration stages is analogous to the dialysate compartment in the diafilter embodiment. The sterile fluid in the common space is then back-filtered into the fiber lumens of the second (redundant filtration) stage. The sterile fluid then exits the cartridge at the header outlet port. This design advantageously provides the safety of redundant filtration, assuring sterility, in the convenience of a conventional single bundle cartridge.

Other features and advantages of the present invention will be apparent from the following detailed descriptions when read in conjunction with the accompanying drawings.

DETAILED DESCRIPTION OF PREFERRED EMBODIMENTS

Figure 1:
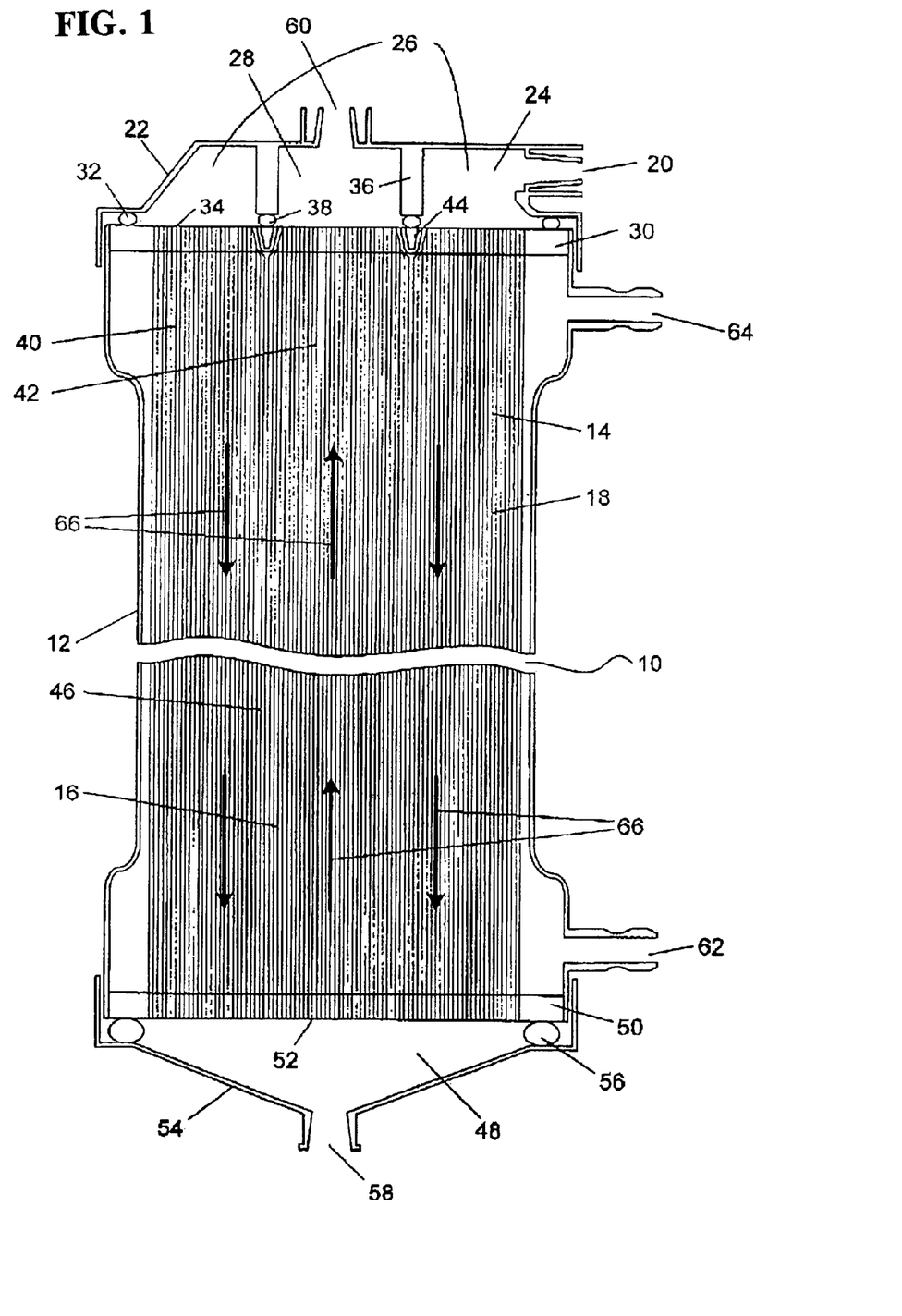
FIG. 1 is a schematic, cross-sectional view of the single bundle filtration cartridge for use as a diafilter in accordance with one embodiment.

Reference is made to FIG. 1, which schematically illustrates a cross-sectional view of a mid-dilution hemodiafiltration cartridge 10 in accordance with one embodiment. Cartridge 10 includes a housing 12, which defines a first stage 14 and a second stage 16, as will be described in greater detail hereinafter. Housing 12 is preferably cylindrical in shape and is formed of a rigid plastic material. Housing 12 contains a longitudinal bundle of semi-permeable hollow fibers 18, as are known in the art. The semi-permeable hollow fibers 18 serve as a means for transferring the toxins, which are being removed, from the blood flowing through the inner lumen portions of the fibers 18. Any number of semi-permeable hollow fibers 18 that are commercially available for this intended purpose may be used. For example, semi-permeable hollow fibers 18 come in variety of dimensions and can be formed of polymers, such as polysulfone, or be cellulose-based.

In an embodiment of the present invention, cartridge 10 is adapted to operate in conjunction with a hemodiafiltration machine, such as the Fresenius 4008 On-Line Plus or Gambro AK 200 Ultra or a modified hemodialysis machine, such as the Fresenius 2008H, Cobe Centry System 3, or Baxter SPS 1550.

During operation, blood transferred from the patient, via a blood pump and bloodlines, enters the first stage 14 of cartridge 10 through an inlet port 20 which is preferably integrally formed in a header cap 22 mounted on a first end of housing 12. The header cap 22 defines an inner header space 24, which is actually divided into a first inner header space 26 and a second inner header space 28. Because the header cap 22 is preferably circular in shape, the first and second inner header spaces 26, 28 are likewise each circular in shape. In this embodiment, the first inner header space 26 is in the form of a ring surrounding the second inner header space 28. The first inner header space 26 may be referred to as an arterial blood space and the second inner header space 28 may be referred to as a venous blood space. As will be explained in greater detail hereinafter, the first and second inner header spaces 26, 28 are associated with the first and second stages 14, 16, respectively.

Both the first and second inner header spaces 26, 28 are separated from the rest of the cartridge 10 by a first potting compound 30, which forms a seal around the outside surfaces of the hollow fibers 18 at the first end of the housing 12. As shown the header cap 22 can be a removable type that may be threaded on to the casing 12. The internal header space 24 is sealed from the external environment by an O-ring 32, which seals against the potting compound 30. It can be appreciated by one skilled in the art, that the header cap 22 could also be attached permanently in this configuration as well as by several other methods, such as a snap-fit type construction.

Blood enters the first inner header space 26 through the inlet port 20, preferably in a tangential flow direction so as to more equally perfuse the first inner header space 26 before the blood enters the hollow fibers 18 at an interface 34. Interface 34, in this embodiment, is an upper surface of the potting compound 30. Interface 34 preferably includes a polyurethane interface structure. The first inner header space 26 can be separated from the second inner header space 28 by several techniques. For example, as illustrated in FIG. 1, the first inner header space 26 may be separated from the second inner header space 28 by an annular wall 36 which partitions the inner header space 24 into the first and second spaces 26, 28, respectively. Preferably, the inner wall 36 is formed as an integral part of the header cap 22. The inner wall 36 extends inwardly toward the fibers 18 from an inner surface of an upper portion of the header cap 22. To provide a seal between the first and second inner header spaces an internal O-ring 38 is preferably included. In the illustrated embodiment, the internal O-ring 38 is disposed at the end of the inner wall 36 opposite to where it attaches to the header cap 22. The internal O-ring 38 provides a sealing action when the header cap 22 interfaces with the interface 34.

In accordance with the present invention, portions of the hollow fibers 18 are separated into first and second sections, generally indicated at 40, 42, respectively. It can be appreciated that the first fiber section 40 is defined by a plurality of individual hollow fibers 18 and similarly, the second fiber section 42 is defined by a plurality of individual hollow fibers 18. The first fiber section 40 fluidly communicates with the first inner header space 26 and the second fiber section 42 fluidly communicates with the second inner header space 28. The separation of the hollow fibers 18 can be accomplished using a number of different techniques, including but not limited to inserting a separator 44 into the bundle of hollow fibers 18 at the first end of the housing 12 prior to the potting process.

In one exemplary embodiment, the separator 44 is in the form of an annular ring made of a suitable material, such as a plastic material. The separator 44 divides the single cylindrical hollow fiber bundle 18 into the first fiber section 40 (referred to herein as an external fiber bundle ring) and the second fiber section 42 (referred to herein as an internal cylindrical fiber bundle) at the first ends of the fibers 18. In other words, the external fiber bundle ring 40 surrounds the internal cylindrical bundle 42. The separator 44 may also serve a dual purpose as an O-ring seat for the internal O-ring 38. The external fiber bundle ring 40 constitutes an arterial fiber bundle and the internal cylindrical fiber bundle 42 is referred to herein as a venous fiber bundle. The arterial fiber bundle 40 fluidly communicates with the first inner header (arterial) space 26 and the venous fiber bundle 42 fluidly communicates with the second inner header (venous) space 28.

During the potting process, the separator 44 may be encased in the first potting compound 30. The separator 44 is preferably made of a relatively non-rigid plastic, such as polyethylene, that may be trimmed flush with the first potting compound 30.

As blood enters the first inner header space 26 through the inlet port 20, the blood traverses down the inside of the arterial fibers 40 that are disposed within a filtration space (dialysate compartment) 46 of the diafilter where diafiltration occurs. The outsides of the arterial fibers 40 are immersed in dialysate. This results in first stage hemodiafiltration of toxins, i.e., both filtration and diffusion, which takes place along the entire length of the arterial fibers 40 within filtration space 46. This results in the blood being partly hemodiafiltered, in other words, removal of some of the toxins present in the blood is achieved in this first stage. In an embodiment of the present invention, a significant portion, e.g., approximately 20%–60%, of the plasma water is filtered as the blood flows through the first stage 14. The partly hemodiafiltered blood exiting the arterial fibers 40 enters an inter-stage header space 48 associated with another end of the housing 12. The blood entering the inter-stage header space 48 is in a hemoconcentrated state, i.e., the level of hematocrit in the blood is increased. In accordance with an embodiment of the invention, the filtration space 46, common to both the first stage 14 and the second stage 16 is separated from the inter-stage header space 48, for example, by a second potting compound 50, in analogy to the separation described above with reference to the inner header space 24 and the first potting compound 30.

The inter-stage header space 48, which acts as a transition stage for blood exiting the first stage 14 and entering the second stage 16, is defined by a second header cap 54 which is preferably made from rigid plastic material and is attached to the second end of housing 12. In this illustration, the second header cap 54 is of a removable type and attached to the casing 12 by screw threads. It will be appreciated by one skilled in the art that the header cap 54 can be attached in several ways, including a snap-fit technique. The inter-stage header space 48 can be sealed from the external environment with a second O-ring 56. As shown in FIG. 1, the second O-ring 56 is disposed between the polyurethane interface 52 and the second header cap 54.

In operation, the blood is pumped through the inlet port 20 through the first inner header space 26 and into the arterial fibers 40. The pressure at the inlet port 20 is thus higher than other locations of the diafilter. The blood will naturally flow toward an area of lower pressure and therefore, the blood flows toward the inter-stage header space 48.

The blood residing in the inter-stage header space 48 prior to entering the second stage 16, is diluted with a physiological sterile solution that enters cartridge 10 via header inlet port 58. The blood in the inter-stage header space 48 is hemodiluted, i.e., the blood hematocrit level is decreased.

Because the second inner header space 28 is at a lower pressure compared to the first stage and the inter-stage header space 48, the hemodiluted blood enters the venous fibers 42, disposed in the second stage 16, and is then carried by the venous fibers 42, in a manner similar to that described above with reference to the first stage 14, to the second inner header space 28. Further hemodiafiltration takes place along the length of these venous fibers 42 until the blood exits into the second inner header space 28 (venous space) of the first header cap 22 and out of an outlet port 60 formed in the first header cap 22. The outlet port 60 represents a location of low pressure compared to the other locations of the diafilter, including the inlet port 20 that represents a location of the highest pressure, and therefore, the hemodiluted blood flows from the inter-stage header space 48 to the outlet port 60. The outlet port 60 is referred to as a venous port. The venous port 60 may be of the same type as the inlet port 20, e.g., a standard twist lock connector. As the hemodiluted and partly hemodiafiltered blood flows through the venous fibers 42, additional toxins are removed from the blood by diffusion and filtration and thus, as the blood is discharged into the second inner header space 28, the blood is in a hemodiafiltered state.

In an embodiment of the present invention, the blood is diafiltered by cartridge 10 at such a rate so that upon exiting the second stage 16, via the venous port 60, the blood hematocrit level is substantially the same as that of the blood entering the first stage 14 through the inlet port 20. As in standard hemodialysis processes, small changes in the blood hematocrit level may be required in order to control the net ultrafiltration, and maintain patient fluid balance.

The dialysate flow and connections are preferably the same as in standard dialysis processes. Dialysate enters the cartridge 10 through a dialysate inlet port 62, e.g., a standard Hansen connector as is known in the art. The dialysate in the present invention perfuses and flows through the filtration space 46 around the outside of the hollow fibers 18. The dialysate exits the cartridge 10 through a dialysate exit port 64. Preferably, the dialysate inlet port 62 and the dialysate exit port 64 are the same type of port, e.g., Hansen connector. Dialysate is pumped into the inlet port 62 which represents a location of high pressure, while the exit port 64 represents a location of low pressure and therefore the dialysate flows in a direction from the inlet port 62 to the exit port 64.

In an embodiment of the present invention, the dialysate flows in one direction from the inlet 62 to the outlet 64. Since the filtration space (dialysate compartment) 46 is common to both stages, dialysate runs counter-current to the blood in the first stage 14 and co-current to the blood in the second stage 16. In the first stage 14, the blood flows from the inner header space 26 towards the second potting compound 50 flowing through the inter-stage header space 48 before entering the second stage 16 at the potting interface 52 and then flowing toward the venous exit port 60 due to the pressure differential of the system. Filtration takes place from the blood to the dialysate across the semi-permeable wall of the hollow fibers 18 (both the arterial and venous fibers 40, 42). The overall filtration rate is a function of the dialysate outflow and replacement fluid inflow and advantageously is significantly greater than is achievable in conventional post-dilution hemodiafiltration. According to one embodiment of the present invention, the overall filtration rate is from about 25% to about 85%, preferably from about 40% to about 60% of the blood flow rate. These flows can be controlled by pumps within a conventional hemodiafiltration machine.

The relative filtration rates of the first and second stages 14, 16 may be passively controlled by the relative of transmembrane pressure (TMP) between the blood compartments 40, 42 and the filtration space (dialysate compartment) 46 which is dependent upon factors, such as hemoconcentration, blood viscosity, within each blood compartment. For example, the blood in the first stage 14 is hemoconcentrated and more viscous, but at high pressure, while the blood in the second stage 16, is hemodiluted and less viscous and at low pressure. As pressures become stabilized, a higher relative filtration rate may be realized in the second stage 16.

Manufacture of the cartridge 10 in this illustration can be similar to the manufacture of a hemodialyzer (not shown). The bundle of hollow fibers 18 is disposed within the housing 12. The separator 44 is inserted into the first end of the hollow fibers 18. Subsequently, standard potting techniques may be followed resulting in potting compound being injected through the dialysate inlet and exit ports 62, 64 while the cartridge 10 is spun in a centrifuge to form the first and second potting compounds 30, 50. The header caps 22, 54 are attached to the housing 12 using any number of suitable techniques, including but not limited to screw threads. A removable header design has an advantage in reuse of the diafilter; allowing for easier removal of clotted material or debris formed on either or both the potting interfaces 34, 52. Reprocessing of the diafilter is similar to standard dialyzers in that the blood inlet port 20 and outlet port 60 and dialysate inlet and outlet ports 62, 64 are connected to a dialyzer reuse machine. The only constraint is that the substitution inlet port 58 is capped.

For purpose of illustration, the blood flow within the cartridge 10 according to one embodiment is indicated by arrows 66.

Figure 2:
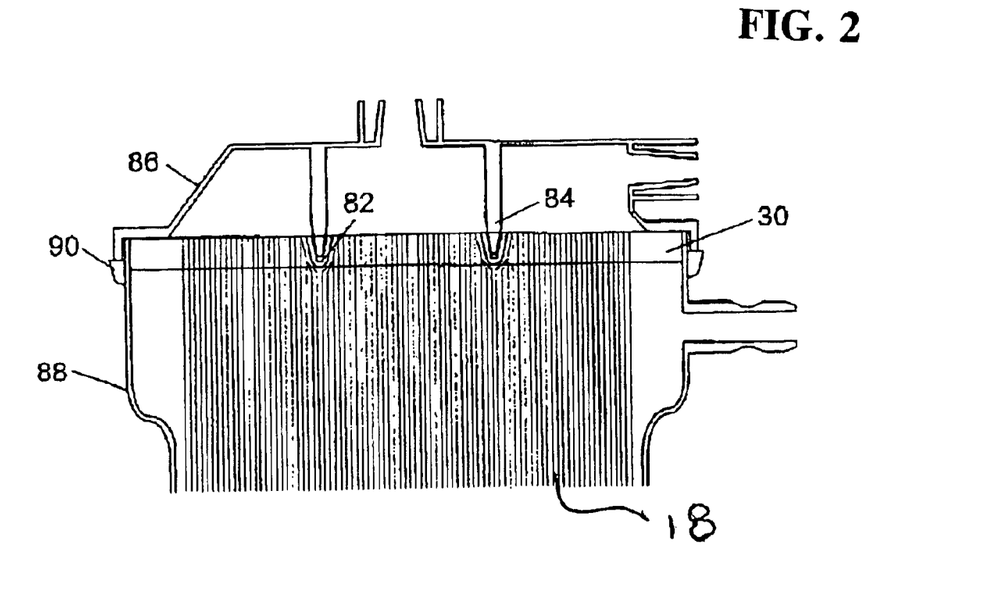
FIG. 2 is a cross-sectional view of an end cap according to one embodiment for use with the diafilter of FIG. 1.
Figure 3:
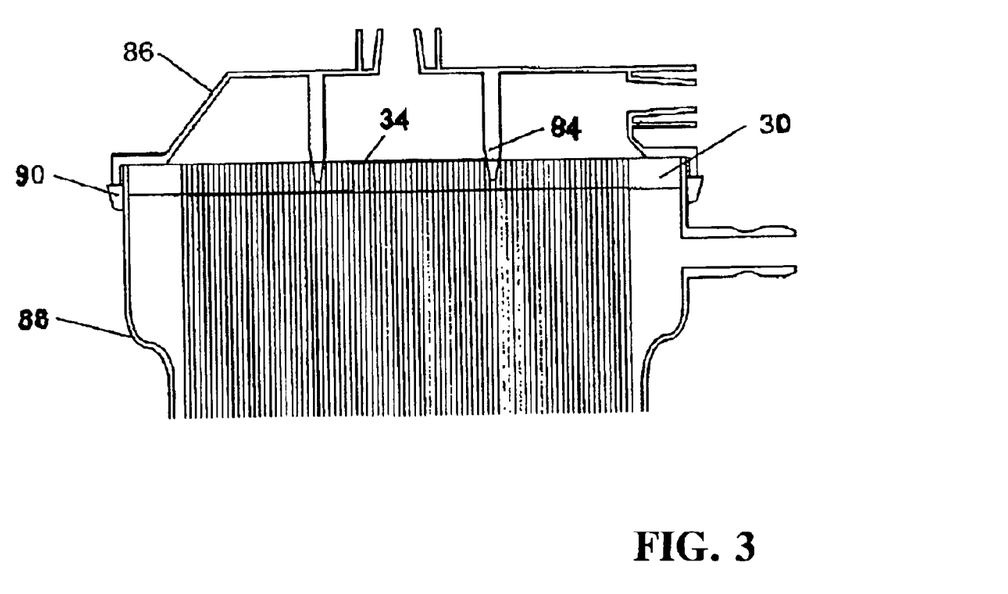
FIG. 3 is a cross-sectional view of an alternative end cap for use with the diafilter of FIG. 1.

Reference is now made to FIGS. 2 and 3, which illustrate alternate methods of separating the fibers 18 and attaching the two-port header cap to form the two stages. Operation of the diafilter is the same as only the methods of manufacture differ.

In FIG. 2, the separating ring 82 is designed with a hollow core. When the ring 82 and the polyurethane 30 are trimmed off after the potting process is performed, the core is opened so that a channel in the ring 82 is available. An inner wall 84 is provided and extends inwardly from header cap 86. In this embodiment, the inner wall 84 has an annular shape; however, other shapes are possible. The inner wall 84 has an extended tip that inserts into and can be welded or bonded to the internal surfaces of the separating ring 82. In other words, the extended tip is received in the channel of the ring 82 and acts to secure and locate the extended tip. In this illustration the header cap 86 is also fixedly attached to a casing (housing) 88. The header cap 86 is bonded or welded to a circumferential ring 90 on the casing 88 such that it seals the internal header space from the external environment. Preferably the internal and external bonds occur simultaneously for manufacturing ease.

In FIG. 3, the connection of the header cap 86 to the casing 88 is the same as in FIG. 2. The difference is in the seal of the internal wall 84. In this illustration the tip of the internal wall 84 seals directly into the potting compound 30. One skilled in the art can appreciate that several methods can be used for this. Some examples are: warming the polyurethane till soft and pressing the tip into the interface 34, then allowing the polyurethane to cool and seal around the wall 84; and alternatively, cutting a thin annular ring into the potting compound 30 then sealing the wall tip into the annulus with either a bonding agent or by press fit.

The header attachment method illustrated in FIG. 3 does not require a separator to be inserted into the fiber bundle prior to potting, as such the potting process is advantageously equivalent to that of a standard dialyzer for this technique. The disadvantage of this design is that a small annular ring of fiber that otherwise could have been used to filter the blood is sealed off by the internal wall 84. These fibers are essentially unused fibers.

Figure 4:
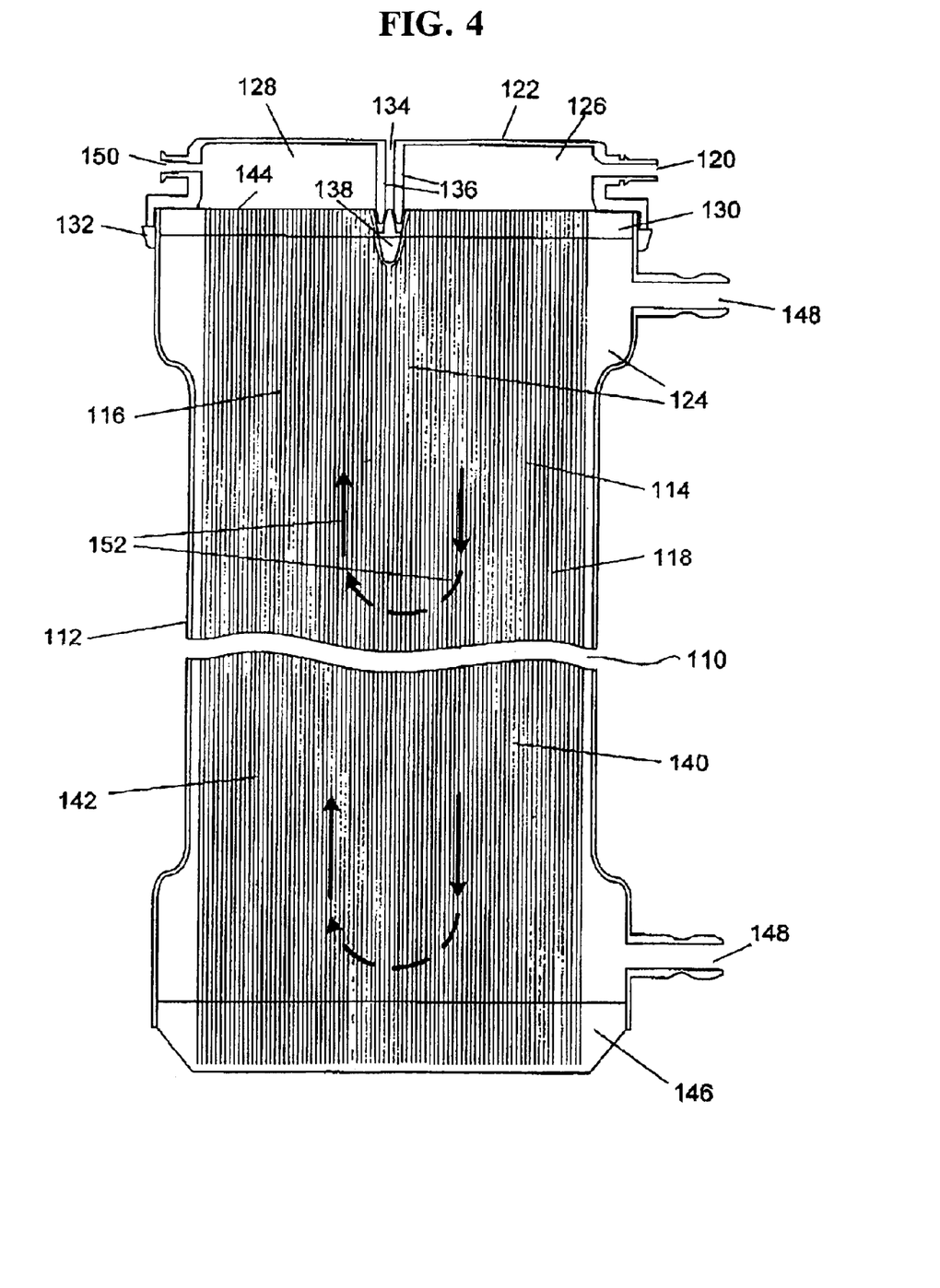
FIG. 4 is a schematic, cross-sectional view of a single bundle filtration cartridge for producing sterile infusion fluid in accordance with one embodiment.

Reference is made to FIG. 4, which schematically illustrates a cross-sectional view of a cartridge 110 used as a sterilization filter according to one embodiment. The cartridge design is similar to the diafilter embodiment with the exception that the ends are configured differently.

The cartridge 110 includes a housing 112, which defines a primary filtration stage 114 and a redundant filtration stage 116. As in the diafilter embodiment, the housing 112 is preferably cylindrical and contains a longitudinal bundle of semi-permeable hollow fibers 118. As previously-mentioned, the fibers 118 come in a variety of dimensions and can be formed of several different materials. The fibers 118 serve as a means for filtering out bacteria and endotoxin from the incoming fluid resulting in sterile infusion quality fluid. The cartridge 110 may be used in any application where sterile fluid is required, including on-line hemodiafiltration to name just one exemplary application.

In operation a physiologic fluid, such as dialysate, enters into the primary filtration stage 114 through an inlet port 120, which is preferably integrally formed in the header cap 122 mounted on the first end of the housing 112. The inlet port 120 may be any type of suitable fluid connection port. Once mounted the header cap 122 defines two internal header spaces, a primary inner header space 126 and a secondary inner header space 128. The primary and secondary header spaces 126, 128 assume a semicircular shape in this embodiment and are associated with the primary 114 and redundant 116 filtration stages respectively. The primary and secondary header spaces 126, 128 are not limited to having a semi-circular shape but rather these spaces 126, 128 can assume any number of different shapes. For example, it will be appreciated by one skilled in the art that the fiber bundle in the sterilization filter embodiment could be separated into annular stages rather than semi-circular ones. This would result in the formation of concentric stages. The shape of the stages is not critical to the performance of the sterilization filter; therefore a variety of shapes can be used.

The inner header spaces 126, 128 are segregated from a filtration space 124 of the cartridge 110 by a first potting compound 130 that seals around the outside of the fibers 118 and the inside end of the housing 112.

As shown, the header cap 122 is fixedly attached to the housing 112 by a weld or bond to a circumferential ring 132 on the outside of the casing. This bond provides one of the seals from the external environment for the internal header spaces 126, 128. It can be appreciated by one skilled in the art that the permanent attachment of the header 122 to the casing 112 can be accomplished in several ways. It can also be appreciated that the header could be attached in a removable way with O-ring seals similar to an illustration of the diafilter embodiment of FIG. 1. However, it can also be appreciated by one skilled in the art that the sterilization filter not being used with blood obviates the need for a removable header.

In the illustrated embodiment, the seals separating the inner header spaces from each other also serve as the second seal from the external environment. As illustrated, the header cap 122 has two integrally formed internal walls 136 that span an internal cross-section of the header cap 122. In between the two walls 136 is an open slot 134, which also spans across a cross-section of the header cap 122 and is open to the environment. Each internal header space 126, 128 is sealed from both the environment and each other when the distal tips of the internal walls 136 are bonded or welded or otherwise attached to a two cavity fiber separating rib 138. The separating rib 138 extends across a cross-section of the housing 112. As with the separating ring 44 for the diafilter of FIG. 1, the separating rib 138 serves a dual purpose. Prior to potting the rib 138 separates the hollow fibers 118 into a first fiber section 140 and a second fiber section 142. After potting the rib 138 is trimmed with the polyurethane thereby opening up two channels, which serve as the sealing sites for the walls 136 of the internal header spaces 126, 128.

Non-sterile physiologic fluid is pumped through inlet 120 and enters the first header space 126 where it then enters the fibers 118 of the first section 140 through the potting interface 144. The inlet 120 is a location of high pressure due to the fluid being pumped into the inlet 120 under pressure. This first fiber section 140 makes up the primary filtration stage 114. The fluid flows into the fibers 118 and across the fiber membrane of each fiber 118, which effectively removes the bacteria and endotoxin from the fluid. All the fluid is forced across the fiber membranes since the opposite ends of the hollow fibers 118 have been sealed off by a second potting compound 146. The fluid flowing with the first fiber section 140 is conducted across the fiber membranes due to an existing pressure differential in which the area surrounding the fibers of the first fiber section 140 is at a lower pressure compared to the pressure inside of the fibers 118 of the first section 140.

The now sterile filtered fluid resides in the internal casing space 124 around the hollow fibers 118. This space 124 is analogous to the dialysate compartment in the diafilter embodiment of FIG. 1. However, during operation of the sterilization filter, the casing ports 148 remain sealed off to prevent any communication of the sterile fluid with the environment. The pressure within the space 124 then moves the fluid into the fibers 118 of the second section 142. The fluid crosses the membrane of these fibers 118 into the fiber lumen and is filtered a second time. As such the second fiber section 142 makes up the redundant filtration stage 116.

Twice filtered sterile fluid then exits into the second internal header space 128 and out of a header outlet port 150. The outlet port 150 is a lower pressure than other locations of the filter and thus, the fluid is caused to flow according to the aforementioned flow path as the fluid entering the fibers 118 of the first section 140 is conducted across two separate fiber membranes in order to flow into the second internal header space 128 and ultimately through the outlet port 150. The outlet port 150 may be of any type readily adaptable to an IV infusion set (e.g. a luer port). The general flow of fluid in the sterilization cartridge is depicted by the arrows 152. The solid arrows indicate inter-lumen fluid flow, while the broken line indicated flow between the stages.

The internal walls 136 and separating rib 138 may be configured a number of different ways by one skilled in the art. However, as illustrated in FIG. 4, the design has a particular safety feature. A potential danger in a header cap with two compartments, a non-sterile inlet fluid one 126 and a sterile fluid outlet one 128, is shunting of flow between the two compartments and potential contamination of the outlet flow. This is alleviated not only by two distinct seals separating the compartments, but also by the presence between the two seals of the open slot 134. If either seal were to fail it would be indicated by fluid exiting the open slot 134, the path of least resistance, rather than potentially being transferred to the other compartment.

The casing ports 148, sealed during normal operation of the filter may be used for priming and testing. The ports 148 may be of any type suitable for making a leak free connection including Hansen ports as in the diafilter embodiment. During a priming operation, sterile fluid can be pumped into ports 148 where it will force air out of the filtration chamber 124 and fiber lumens 118 and eventually exit out of the two header ports 120, 150. The design allows for this advantageous methodology whereas priming via the inlet port 120 could result in trapped air in the fibers 118 due to them being plugged at one end. The ports are also used in order to detect fiber leaks, such as performing an air pressure decay test. By pumping air into the filtration chamber 124 one can advantageously test the fiber 118 of both filtration stages 114, 116 simultaneously.

Figure 5:
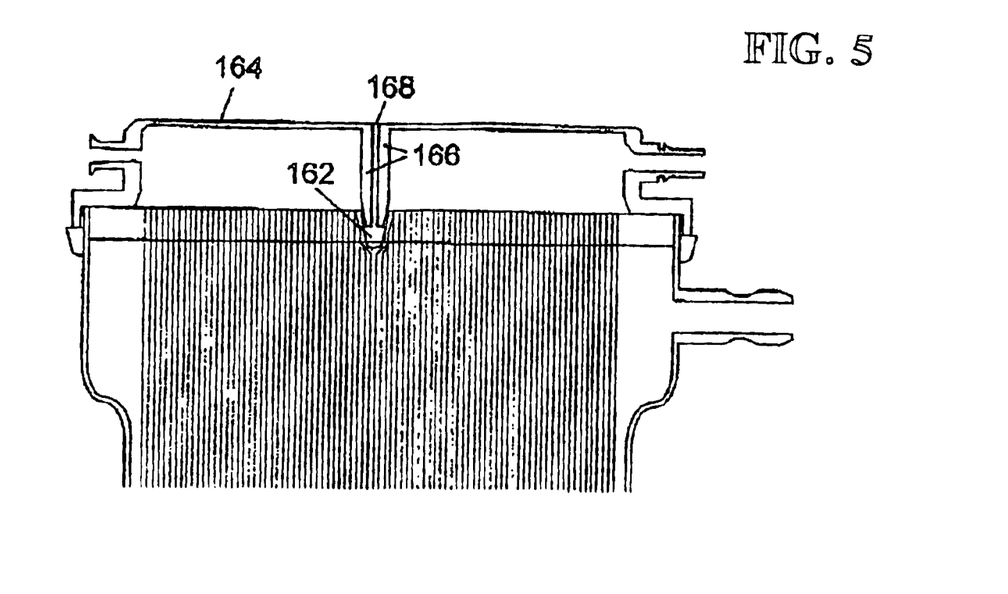
FIG. 5 is a cross-sectional view of an end cap according to one embodiment for use with the filtration cartridge of FIG. 4.
Figure 6:
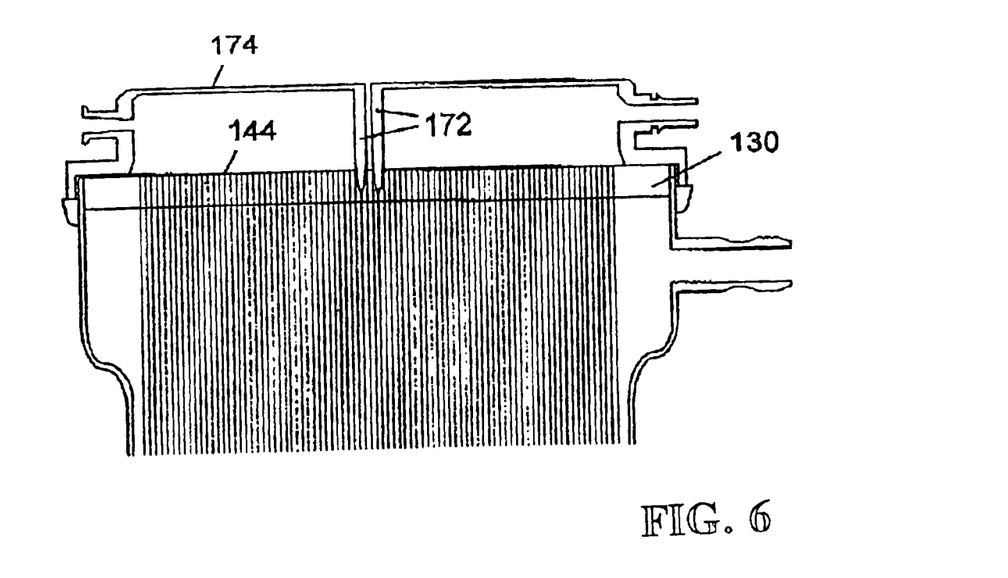
FIG. 6 is a cross-sectional view of an end cap according to another embodiment and for use with the filtration cartridge of FIG. 4.

Attention is now given to FIGS. 5 and 6 which illustrate two additional designs for attaching the header to the casing end. It will be appreciated by one skilled in the art that several additional methods are available as well.

FIG. 5 shows a spacing rib 162 with a single channel core rather than a double channel as illustrated in FIG. 4. As a result the internal wall tips 166 of the header 164 only bond to the spacing rib 162 on their outside surfaces. There is no bond on the interior channel surface 168.

FIG. 6 shows a configuration in which there is no spacing rib. As a result the potting process is simplified and the same as that of a standard dialyzer. The tips of the internal walls 172 of the header 174 are designed such that they seal directly into the polyurethane 130. As in the diafilter embodiment several methods could be employed for achieving this seal, including: warming the polyurethane at the interface 144 till soft then pressing the tips into it, and cutting a channel into the potting compound 130 and sealing the tips by bonding or press fit. With either technique, some of the fibers along the central separating line, including those in the open slot 134 area, will be sealed off and not used for filtration.

It will be appreciated by persons skilled in the art that the present invention is not limited to the embodiments described thus far with reference to the accompanying drawings. Rather the present invention is limited only by the following claims.

What is claimed:

1. In a blood dialysis system including a source of substitution fluid and a blood dialysis machine, a hemodiafiltration cartridge comprising:
   a housing including a blood inlet which receives blood, a blood outlet which discharges diafiltered blood, a dialysate inlet for receiving a dialysate fluid and a dialysate outlet for discharging the dialysate fluid, the housing further including a plurality of semi-permeable filtering elements;
   a member for dividing the housing into a first hemodiafiltration stage and a second hemodiafiltration stage, a first portion of the plurality of semi-permeable filtering elements being associated with the first stage and a second portion of the plurality of semi-permeable filtering elements being associated with the second stage, the blood inlet being in fluid communication only with the first stage, while the blood outlet is in fluid communication only with the second stage; and
   an inter-stage section for providing fluid communication between the first and second stages, the inter-stage section including an inlet for receiving a substitution fluid, wherein blood entering the blood inlet is partially diafiltered as it flows within the semi-permeable filtering elements of the first stage before being discharged into the inter-stage section where it is mixed with substitution fluid to form a blood/substitution mixture which then flows within the semi-permeable filtering elements of the second stage where further diafiltration occurs, wherein the housing includes only one dialysate fluid compartment that is common to both the first and second stages.

2. The system of claim 1, wherein the blood flows in a first direction in the first stage and in a second direction in the second stage.

3. The system of claim 2, wherein the dialysate fluid flows in the second direction relative to both the first and second stages.

4. The system of claim 1, wherein the housing includes a detachable first header cap disposed at a first end of the cartridge, the member including an inner wall formed as part of the first header cap, the inner wall dividing the first header cap into first and second inner header spaces.

5. The system of claim 4, wherein the first header cap includes the blood inlet which is in fluid communication with the first inner header space.

6. The system of claim 4, wherein the first inner header space is only in fluid communication with the filtering elements of the first stage, the second inner header space only being in fluid communication with the filtering elements of the second stage.

7. The system of claim 4, wherein the member includes a separator which divides the plurality of the filtering elements into the first and second stages.

8. The system of claim 7, wherein the separator comprises an annular ring disposed in a first potting compound at a first end of the plurality of filtering elements proximate to the blood inlet and blood outlet.

9. The system of claim 7, wherein the inner wall is aligned with the separator.

10. The system of claim 7, further including an O-ring disposed between the inner wall and the separator for sealing the first inner header space from the second inner header space.

11. The system of claim 7, wherein the separator includes a channel formed therein, the inner wall having a distal tip section which is attached to the separator within the channel.

12. The system of claim 1, further including a first potting compound surrounding the plurality of filtering elements at a first end thereof, and wherein the member comprises an inner wall of a first header cap that is connected to a first end of the housing, a distal tip section of the inner wall being disposed within the first potting compound so as to divide the plurality of filtering elements into the first and second stages.

13. The system of claim 4, wherein the blood outlet is formed in the first header cap so to be in fluid communication only with the second inner header space.

14. The system of claim 1, further including a second header cap disposed at one end of the plurality of filtering elements so as to partial define the inter-stage connector, the second header cap having the substitution fluid inlet formed therein.

15. The system of claim 14, further including a second potting compound at the one end of the plurality of filtering elements, the second potting compound permitting each of the filtering elements to be in fluid communication with the inter-stage section.

16. The system of claim 1, further including a dialysate compartment defined by the housing and surrounding the filtering elements of the first and second stages, the dialysate inlet and outlet being in fluid communication with the dialysate compartment.

17. In a blood dialysis system including a source of substitution fluid, a blood dialysis machine, and a hemodiafiltration cartridge, the cartridge comprising:

a housing including a blood inlet which receives blood, a blood outlet which discharges diafiltered blood, a single dialysate inlet for receiving a dialysate fluid and a single dialysate outlet for discharging the dialysate fluid;

a member for dividing the housing into a first hemodiafiltration stage and a second hemodiafiltration stage, wherein the member permits the blood inlet to be in fluid communication only with the first stage while fluid communication is prevented between the blood inlet and the second stage, the blood outlet being in fluid communication only with the second stage, the dialysate flowing within a dialysate fluid compartment common to both the first and second stages and in communication with the single dialysate inlet and outlet;

a first filtering element associated with the first stage;

a second filtering element associated with the second stage; and an inter-stage section for providing fluid communication between the first and second stages, the inter-stage section including an inlet for receiving the substitution fluid, wherein blood entering the blood inlet is partially diafiltered in the first stage before being discharged into the inter-stage section where it is mixed with the substitution fluid to form a blood/substitution mixture which then flows within the second stage where further diafiltration occurs prior to the diafiltered blood being discharged through the blood outlet.

18. A dual-stage hemodiafiltration cartridge, the cartridge comprising:

a housing having a dialysate inlet and dialysate outlet;

a member dividing the housing into a first hemodiafiltration stage which receives blood through a blood inlet and a second hemodiafiltration stage, wherein the housing includes first semi-permeable filtering elements associated with the first stage and second semi-permeable filtering elements associated with the second stage, the member preventing the blood entering the blood inlet from fluidly communicating with the second stage, wherein the housing includes only one dialysate fluid compartment that is common to both the first and second stages;

an inter-stage section for providing fluid communication between the first and second stages, the inter-stage section including an inlet for receiving the substitution fluid, wherein blood entering the inter-stage section from the first stage has a first concentration of toxins, the blood being mixed in the inter-stage section with the substitution fluid to form a blood/substitution mixture which then flows within the second stage, the second stage having a blood outlet through which blood having a second concentration of toxins is discharged, the first concentration of toxins being greater than the second concentration of toxins; and wherein dialysate fluid flow is counter-current to blood flow in the first stage and co-current to blood flow in the second stage.

19. The dual-stage cartridge of claim 18, wherein the housing includes a first header cap disposed at a first end of the cartridge, the member including an inner wall formed as part of the first header cap, the inner wall dividing the first header cap into first and second inner header spaces, the blood inlet being in fluid communication only with the first inner header space, while the blood outlet is only in communication with the second inner header space.

20. The dual-stage cartridge of claim 19, wherein the first inner header space is only in fluid communication with the first semi-permeable filtering elements and the second inner header space is only in fluid communication with the second semi-permeable filtering elements.

21. The dual-stage cartridge of claim 19, wherein the member includes a separator which the divides the plurality of the filtering elements into the first and second stages, the separator cooperating with the inner wall so as to define the first and second stages.

22. The dual-stage cartridge of claim 18, wherein the blood is diafiltered in each of the first and second stages by diffusion of toxins through the first and second semi-permeable filtering elements and by fluid conduction across the first and second semi-permeable filtering elements.

23. A dual-stage filtration cartridge comprising:

a housing having a first sterilization stage including first semi-permeable filtering elements and a second sterilization stage including second semi-permeable filtering elements, the housing having a first end and a second end with the first end including a fluid inlet port and a fluid outlet port and a member that divides the housing into the first sterilization stage and the second sterilization stage, first ends of the semi-permeable filtering elements being proximate to the first end of the housing, second ends of the semi-permeable filtering elements being proximate to the second end of the housing, the fluid inlet port being in fluid communication only with the first sterilization stage, while the fluid outlet port is in fluid communication only with the second sterilization stage, wherein the first and second semi-permeable filtering elements are sealed at the second end of the housing so as to cause the fluid entering the fluid inlet port to flow within lumen sections of the first semi-permeable filtering elements and then be filtered by being conducted across the first semi-permeable filtering elements and then subsequently being filtered again by being conducted across the second semi-permeable filtering elements and into the lumen sections of the second semi-permeable filtering elements prior to being discharged through the fluid outlet port.

24. The dual-stage filtration cartridge of claim 23, wherein the first end of the housing includes a header cap defining an inner header space between the header cap and the first ends of the first and second semi-permeable filtering elements, the member including an inner partitioner formed as part of the header cap and dividing the inner header space into a first inner header space and a second inner header space, the fluid inlet port being in fluid communication only with the first inner header space while the fluid outlet port is in fluid communication only with the second inner header space.

25. The dual-stage filtration cartridge of claim 24, wherein each of the first and second inner header spaces has a semi-circular shape.

26. The dual-stage filtration cartridge of claim 24, wherein the inner partitioner comprises a pair of spaced inner walls extending cross-sectionally across the housing, one of the inner walls defining the first inner header space, the other of the inner walls defining the second inner header space.

27. The dual-stage filtration cartridge of claim 23, wherein the member includes a separating rib disposed at the first ends of the semi-permeable filtering elements so as to divide the semi-permeable filtering elements into the first and second semi-permeable elements.

28. The dual-stage filtration cartridge of claim 24, further including a first potting compound disposed at the first ends of the first and second semi-permeable filtering elements, the first potting compound permitting fluid communication between the first inner header space and the first semi-permeable filtering elements as well as between the second inner header space and the second semi-permeable filtering elements.

29. The dual-stage filtration cartridge of claim 23, further including a second potting compound at the second ends of the first and second semi-permeable filtering elements for sealing off the second ends thereof.

30. The dual-stage filtration cartridge of claim 23, wherein the fluid enters the first stage and is discharged from the second stage both at the first end of the housing.

31. The dual-stage filtration cartridge of claim 23, wherein the first sterilization stage is independent from the second sterilization stage such that the second sterilization stage is a redundant sterilization stage with the fluid being completely filtered in each of the stages.

32. A method of hemodiafiltration comprising the steps of:
    receiving a blood inflow;
    diafiltering said blood inflow in a first stage to provide a partially diafiltered blood outflow;
    mixing said partially diafiltered blood outflow with a substitution fluid to provide a blood/substitution fluid mixture; and
    diafiltering said blood/substitution fluid mixture in a second stage, wherein both the first and second stages are included in a single cartridge housing and the dialysate fluid flows in a compartment that is common to both the first and second stages.

33. A method of hemodiafiltration comprising the steps of:
    receiving a blood inflow;
    diafiltering said blood inflow in a first stage to provide a blood outflow having a first concentration of toxins;
    mixing said partially diafiltered blood outflow with a substitution fluid at an inter-stage section to provide a blood/substitution fluid mixture; and
    diafiltering said blood/substitution fluid mixture in a second stage to produce blood having a second concentration of toxins, the first concentration being greater than the second concentration, wherein dialysate fluid is common to both the first and second stages and is received within only a single dialysate inlet formed in a housing containing the two stages and is discharged through only a single dialysate outlet formed in the housing.

34. The method of claim 33, further including the steps of:
    providing a dual-stage cartridge having a blood inlet at a first end for receiving the blood inflow and the inter-stage connector at a second end, wherein the dialysate fluid flows counter-current to the blood flowing in the first stage and co-current to the blood flowing the in the second stage.

35. A method for filtering a fluid, comprising:
    receiving a fluid at an inlet port of a dual-stage filtration cartridge;
    passing the fluid through a lumen section of a first filtering element;
    conducting the fluid across the first filtering element into an inner cavity of the housing;
    conducting the fluid across a second filtering element and into a lumen section thereof; and
    passing the fluid through the lumen section of the second filtering element to an outlet port through which the fluid is discharged, wherein the inlet and outlet ports are at the same end of the dual-stage cartridge and the first and second filtering elements each includes an open end and a closed end, the closed ends being at the same end of the dual-stage cartridge.

36. The method of claim 35, wherein at least a portion of the fluid flows in a first direction in the first filtering element and at least a portion of the fluid flows in a second direction in the second filtering element, the first and second directions being opposite one another.

* * * * *